US00PP30503P2

(12) United States Plant Patent
Hoogendoorn

(10) Patent No.: US PP30,503 P2
(45) Date of Patent: May 14, 2019

(54) ***ALICEARA* ORCHID PLANT NAMED 'CAMBOELBO'**

(50) Latin Name: ***Nothogenus:* x *Aliceara***
Varietal Denomination: CAMBOELBO

(71) Applicant: ANTHURA B.V., Bleiswijk (NL)

(72) Inventor: Gert-Jan Hoogendoorn, Woubrugge (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,641

(22) Filed: Dec. 7, 2017

(51) Int. Cl.
*A01H 6/62* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of x *Aliceara* plant named 'CAMBOELBO', particularly characterized by having large, purple-red flowers with a large undulated purple-red lip, 1-3 peduncles that are long and sturdy, leaves that are lanceolate and elongated to very elongated, and is propagated by meristem tissue culture is disclosed.

3 Drawing Sheets

Genus and species: *Nothogenus*: x *Aliceara*.
Variety denomination: 'CAMBOELBO'.

BACKGROUND OF THE NEW PLANT

The present invention comprises a new and distinct cultivar of x *Aliceara* plant, botanically known as x *Aliceara* of the Orchidaceae family, and hereinafter referred to by the cultivar name 'CAMBOELBO'.

Miltonia, Oncidium, Brassia and some other genera are a complex group of orchid species that are easily hybridized. The boundaries between the genera have been under discussion for the last several decades. According to the most recent classification by Pridgeon, Cribb, Chase and Rasmussen (Genera Orchidacearum), the plant herein described is most likely a complex hybrid between Miltonia, Oncidium and Brassia species, hence called x *Aliceara*.

All x *Aliceara* plants exhibit a sympodial growth habit. The species typically have 4 to 6 leaves per mature pseudobulb: most of the time one lanceolate leaf with an acute apex grown on the apex of the pseudobulb and four leaves grown from the axis at the base (sympodial growth), with two leaves on each side. The peduncles vary in size from 20-70 cm.

x *Aliceara* orchids are used as flowering potted-plants for home or interiorscape. x *Aliceara* produces upright or pendent lateral racemes or panicles, often with many showy flowers which open in succession beginning with the lowermost. The flowers possess three sepals and two petals, the lateral ones being alike and having a peculiar labellum. Flower colors include various shades of pink, purple, white, yellow, and red-brown.

x *Aliceara* orchids are typically propagated from tissue culture. Asexual propagation of x *Aliceara* is often done from off-shoots which arise from the lower bracts of the inflorescence. The resulting plants are detached from the mother plants and may be planted in a suitable substrate.

The new x *Aliceara* 'CAMBOELBO' is particularly characterized by its attractive and unique large, purple-red flowers with a large, undulated purple-red lip, economical propagation by tissue culture, early flowering, and a plant dimension suitable for packaging and shipping to the market.

'CAMBOELBO' is a product of a planned breeding program conducted by the inventor in Bleiswijk, The Netherlands.

The new x *Aliceara* 'CAMBOELBO' originated from a cross made by the inventor in December 2007 in Bleiswijk, The Netherlands. The female parent is a yellow-green x *Aliceara* pot plant named '60000-0098' (unpatented) and the male parent is a purple-red *Miltonia* pot plant named '60000-0385' (unpatented). A single plant was selected by the inventor from within the progeny of the stated cross-pollination in a controlled greenhouse in Bleiswijk, The Netherlands in December 2010.

Asexual reproduction of 'CAMBOELBO' by meristem tissue culture since 2011 in Bleiswijk, The Netherlands has demonstrated that the new variety reproduces true to type with all of the characteristics, as herein described, firmly fixed and retained through successive generations.

Plant Breeder's Rights for this variety have been applied for in Europe on Nov. 25, 2016. 'CAMBOELBO' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands.

1) Large, purple-red flower with a large, undulated purple-red lip;
2) 1-3 peduncles;

3) Peduncle is long and sturdy;
4) The shape of the leaf is lanceolate and elongated to very elongated; and
5) Plants are propagated by meristem tissue culture.

DESCRIPTION OF THE PHOTOGRAPHS

This new x *Aliceara* plant is illustrated by the accompanying photographs which show the overall plant habit including blooms and foliage of the plant; the colors shown are as true as can be reasonably obtained by conventional photographic procedures. The photographs are of a 70-week old plant grown in a greenhouse in Bleiswijk, The Netherlands in September 2017.

DESCRIPTION OF THE NEW VARIETY

Figure 1:
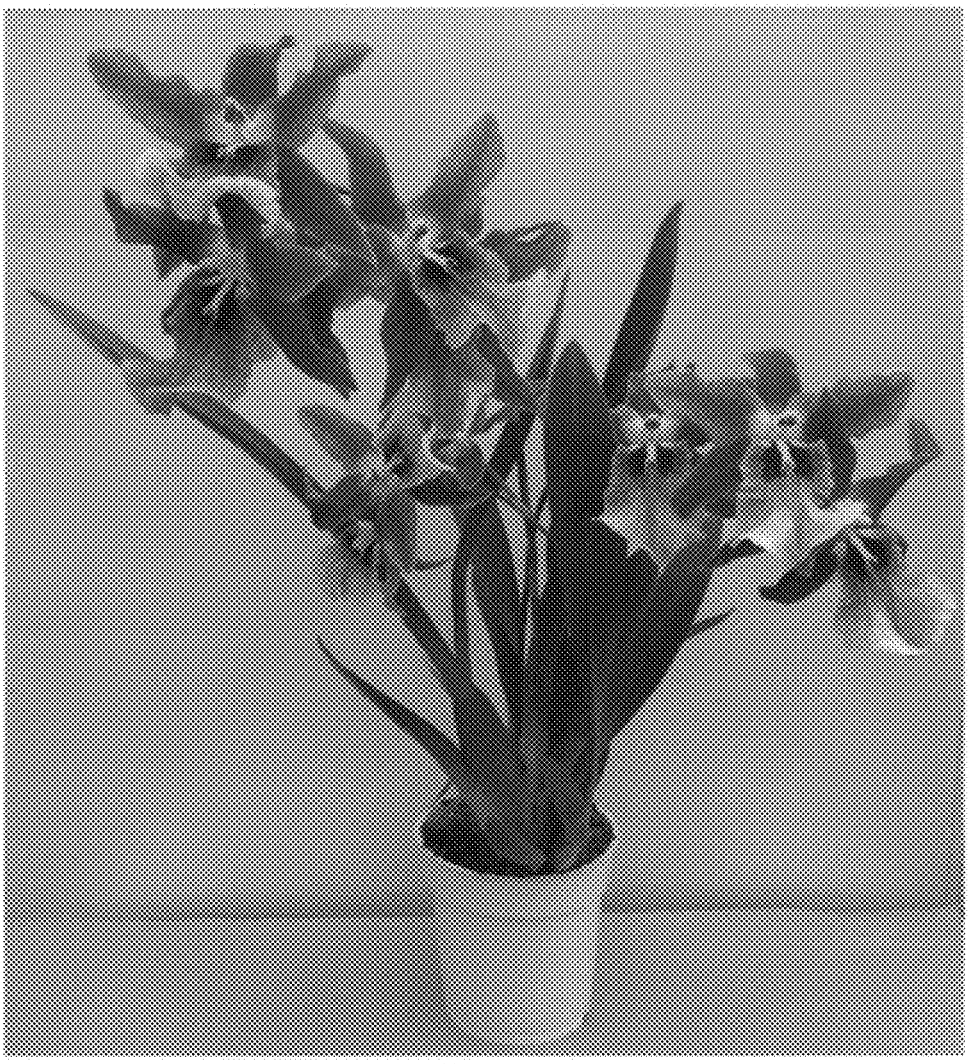
FIG. 1 shows the overall plant habit, including blooms and foliage of 'CAMBOELBO'.
Figure 2:
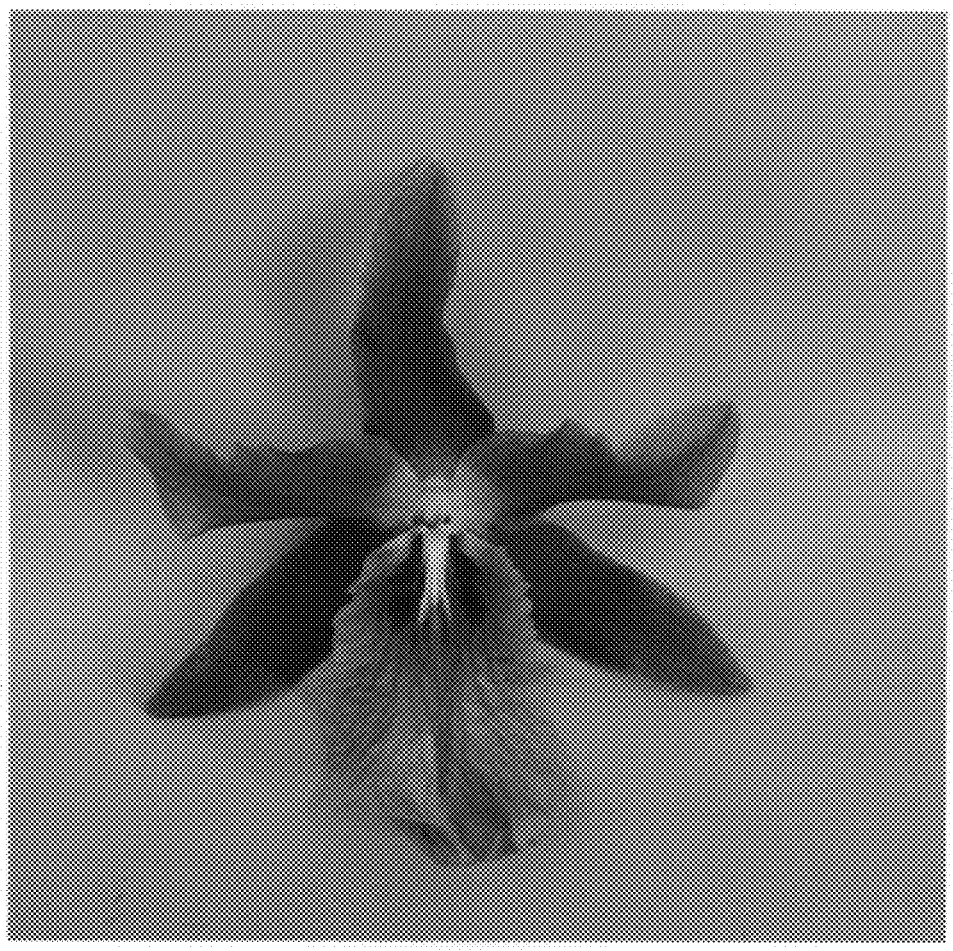
FIG. 2 shows a close-up of a flower of 'CAMBOELBO'.
Figure 3:
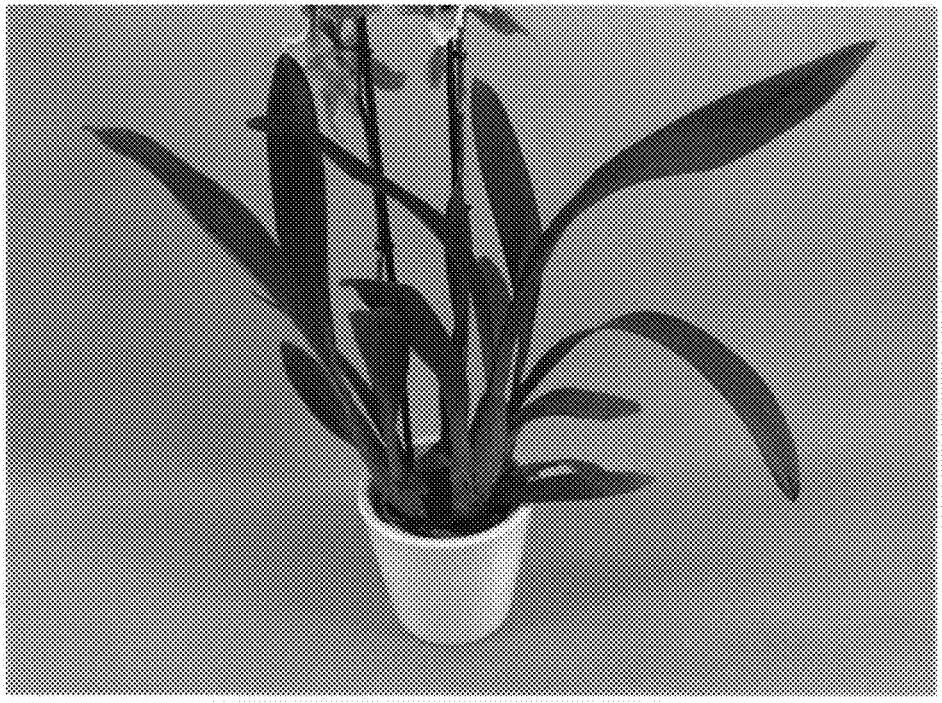
FIG. 3 shows a close-up of the leaves of 'CAMBOELBO'.

The following detailed description sets forth the distinctive characteristics of 'CAMBOELBO'. The data which define these characteristics were collected from asexual reproductions carried out in Bleiswijk, The Netherlands. The plant history was taken on 70-week old plants which were planted from tissue culture to a plug and then to 12 centimeter pots, and grown in a greenhouse between 20° C. to 25° C. Observations were made in September 2017. Color readings were taken under 4000-6000 lux natural light in the greenhouse. Color references are primarily to The R.H.S. Colour Chart of The Royal Horticultural Society of London (R.H.S.) (2015).

DETAILED BOTANICAL DESCRIPTION

Classification:
- *Family*.—Orchidaceae.
- *Botanical*.—x *Aliceara*.
- *Common name*.—Cambria.
- *Variety name*.—'CAMBOELBO'.

Parentage:
- *Female parent*.—x *Aliceara* cultivar '60000-0098' (unpatented).
- *Male parent*.—*Miltonia* cultivar '60000-0385' (unpatented).

Propagation:
- *Type*.—Meristem tissue culture.

Plant:
- *Crop time* (*time to produce a finished flowering plant*).—50 to 70 weeks for a 12 cm pot.
- *Growth habit of peduncle*.—Upright to slightly pendant.
- *Height* (*including pot, including inflorescence*).—65.0 cm to 75.0 cm.
- *Width* (*measured from leaf tips*).—35.0 cm to 45.0 cm.
- *Vigor*.—Strong.

Roots:
- *Root description*.—Greyed-yellow (RHS 164D) colored roots lightly branching with light yellow growing tips (RHS 162D).

Pseudobulb:
- *Number of pseudobulbs*.—1 to 4.
- *Shape*.—Laterally compressed ovoid.
- *Length*.—9.0 cm to 14.0 cm.
- *Width*.—3.5 cm to 4.5 cm.
- *Thickness*.—1.5 cm to 2.5 cm.
- *Color*.—Green (RHS 146B).

Leaves:
- *Mature leaves*.—Quantity per pseudobulb: 4 to 6 leaves are produced before flowering. Length (fully expanded): 25.0 cm to 35.0 cm. Width: 3.5 cm to 4.5 cm. Attitude of the leaves: Erect to semi-erect. Shape: Lanceolate. Base shape: Elongated to very elongated. Apex: Acute. Leaf margin: Entire. Color: Upper surface: RHS 146A. Lower surface: RHS 146B. Texture: Upper surface: Smooth. Lower surface: Smooth. Thickness: 0.4 mm to 0.5 mm. Venation: Pattern: Parallel. Color of the midvein: Upper surface: RHS 146B. Lower surface: RHS 146C.

Peduncle:
- *Quantity per plant*.—1 to 3.
- *Number of flowers per peduncle*.—4 to 7.
- *Length*.—From 54.0 cm to 64.0 cm.
- *Diameter*.—4.5 mm to 5.0 mm.
- *Strength*.—Strong.
- *Aspect*.—Upright.
- *Texture*.—Smooth.
- *Color*.—Green at the base (RHS 144C) and green toward the tip (RHS 144B) with a touch of brown (RHS N199B).
- *Internode length*.—45.0 mm to 55.0 mm.
- *Number of branches*.—0.
- *Callosities*.—None.

Inflorescence description:
- *Appearance*.—Upright, raceme inflorescence with bilaterally symmetrical flowers that open in succession beginning with the lowermost flower.
- *Inflorescence size*.—Height (from base to tip): 170.0 mm to 220.0 mm.
- *Flowering time*.—First flowers can be expected 4 to 8 months after planting in a 12 cm pot.
- *Number of flowers of the inflorescence*.—5 to 7.
- *Flower*.—Height: 95.0 mm to 100.0 mm. Diameter: 83.0 mm to 88.0 mm.
- *Flower longevity*.—On the plant: 3 to 6 weeks.
- *Fragrance*.—Present; smells like lily of the valley. Degree of the fragrance: Moderate.
- *Petals*.—Shape: Elliptic. Apex: Acute. Margin: Undulated. Curvature: Recurving. Curvature of the longitudinal axis: Recurving. Texture: Upper surface: Slightly rough. Lower surface: More smooth. Length (from base to tip): 46.0 mm to 48.0 mm. Width: 19.0 mm to 21.0 mm. Color (when fully opened): Upper surface: Basic color: Red-purple (RHS N79D). Over color: Red-purple (RHS N79C) and white center (RHS 155C). Lower surface: Basic color: Red-purple (RHS N79D). Over color: Greenish-white (RHS 155C) at the base.
- *Dorsal sepal*.—Shape: Elliptic. Apex: Acute. Margin: Entire. Curvature: Recurving. Curvature of the longitudinal axis: Recurving. Texture (both upper and lower surfaces): Leathery, thick, but not shiny. Length (from base to tip): 47.0 mm to 49.0 mm. Width: 17.0 mm to 19.0 mm. Color (when fully opened): Upper surface: Basic color: Red-purple (RHS N79D). Over color: Red-purple (RHS N79C). Lower surface: Basic color: Red-purple (RHS N79D). Over color: Light green (RHS 145C) at the base.

*Lateral sepals*.—Shape: Elliptic. Margin: Entire. Curvature: Recurving. Curvature of the longitudinal axis: Recurving. Texture (both upper and lower surfaces): Leathery, thick, but not shiny. Length (from base to tip): 48.0 mm to 50.0 mm. Width: 10.0 mm to 12.0 mm. Color (when fully opened): Upper surface: Basic color: Red-purple (RHS N79D). Over color: Red-purple (RHS N79B/C). Lower surface: Basic color: Red-purple (RHS N79D). Over color: Light green (RHS 145C) at the base.

*Labellum* (*lip*).—Length: 50.0 mm to 52.0 mm. Width: 38.0 mm to 40.0 mm. Color: Upper surface: Red-purple (RHS N79B/C) and light purple (RHS N80C) toward the margin; few dark red flecks/stripes (RHS 187A) at the base. Lower surface: Red-purple (RHS N79C) and light purple (RHS N80C) toward the margin.

*Apical lobe*.—Shape: Indescribable. Margin: Wavy. Apex: Emarginated. Indentation of apex: Medium. Curvature of the longitudinal axis: Recurving.

*Lateral lobe*.—Size in relation to apical lobe: Smaller.

*Callus*.—Color: Pale-yellow (RHS 160D). Shape: Indescribable. Average size: Indescribable. Average number of protuberance: 2 to 3.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 9.0 mm to 12.0 mm. Diameter: 5.2 mm to 5.5 mm. Color: Light yellow-green (RHS 150D). Wings: Absent.

*Cap*.—Average size: 1.0 mm to 3.0 mm. Shape: Oval cup shape. Color: Light yellow-green (RHS 150D).

*Pollinia*.—Quantity: 2. Diameter: 1.0 mm to 1.2 mm. Color: Yellow-orange (RHS 14B).

*Ovary*.—Length: 26.0 mm to 28.0 mm. Diameter: 2.7 mm to 2.9 mm.

*Pedicel*.—Length: 40.0 mm to 42.0 mm. Diameter: 2.4 mm to 2.6 mm. Color: Green (RHS 144B) and lighter green (RHS144C) toward the flower.

Disease, pest, and stress resistance: No specific resistance or susceptibility observed to date.

Temperature tolerance: Not observed to date.

COMPARISON WITH PARENTAL LINES AND SIMILAR VARIETY

'CAMBOELBO' differs from female parent '60000-0098' (unpatented) in that 'CAMBOELBO' has red-purple flowers with a center pattern and 5 to 7 flowers per plant, whereas '60000-0098' has yellow-green flowers with a flecked pattern and 7 to 9 flowers per plant.

'CAMBOELBO' differs from male parent '60000-0385' (unpatented) in that 'CAMBOELBO' has flowers with a small center pattern, undulated petal margins and 5 to 7 flowers per plant, whereas '60000-0385' has flowers with an even pattern, entire petal margins and 3 to 5 flowers per plant.

'CAMBOELBO' is most similar to the commercial x *Aliceara* plant named 'CAMBLYQE' (U.S. Plant patent application Ser. No. 15/732,645). 'CAMBOELBO' differs from commercial variety 'CAMBLYQE' in that 'CAMBOELBO' has red-purple flowers with a small center pattern and a yellow-green column, whereas 'CAMBLYQE' has light yellow-green flowers with a flecked pattern and a column that is dark red-brown at the base with yellow-green toward the cap. Additionally, 'CAMBOELBO' has a wider lip than 'CAMBLYQE'.

I claim:

1. A new and distinct variety of x *Aliceara* plant named 'CAMBOELBO', substantially as described and illustrated herein.

* * * * *